US008641592B2

(12) United States Patent
Yu

(10) Patent No.: US 8,641,592 B2
(45) Date of Patent: Feb. 4, 2014

(54) METHOD AND DEVICE FOR IMAGE GUIDED DYNAMIC RADIATION TREATMENT OF PROSTATE CANCER AND OTHER PELVIC LESIONS

(76) Inventor: Xinsheng Yu, Columbia, MD (US)

( * ) Notice: Subject to any disclaimer, the term of this patent is extended or adjusted under 35 U.S.C. 154(b) by 834 days.

(21) Appl. No.: 12/729,900

(22) Filed: Mar. 23, 2010

(65) Prior Publication Data

US 2010/0237259 A1    Sep. 23, 2010

Related U.S. Application Data

(60) Provisional application No. 61/210,766, filed on Mar. 23, 2009.

(51) Int. Cl.
*A61N 5/00*    (2006.01)
(52) U.S. Cl.
USPC ............... 600/1; 600/411; 600/407; 600/427; 600/2; 600/3; 600/4; 600/5; 600/6; 600/7; 600/8; 250/492.1; 250/493.1; 250/505.1; 250/492.2; 250/492.3; 378/65; 382/128

(58) Field of Classification Search
USPC ............... 600/411, 407, 1–8, 427; 250/493.1, 250/505.1, 492.1–492.3; 604/500, 427; 378/65; 382/128
See application file for complete search history.

(56) References Cited

U.S. PATENT DOCUMENTS

| 2005/0197564 A1* | 9/2005 | Dempsey ..................... 600/411 |
| 2006/0193441 A1* | 8/2006 | Cadman ........................ 378/153 |
| 2007/0043286 A1* | 2/2007 | Lu et al. ........................ 600/407 |
| 2010/0016649 A1* | 1/2010 | Prionas et al. ................... 600/1 |
| 2010/0094119 A1* | 4/2010 | Yu et al. ........................ 600/411 |
| 2010/0239066 A1* | 9/2010 | Fahrig et al. ..................... 378/65 |

OTHER PUBLICATIONS

Tomas Kron, David Eyles, Schreiner L John, and Jerry Battista. Magnetic resonance imaging for adaptive cobalt tomotherapy: A proposal, J Med Phys. Oct.-Dec. 2006; 31(4): 242-254.*

* cited by examiner

*Primary Examiner* — Christine Matthews
*Assistant Examiner* — Sunita Reddy
(74) *Attorney, Agent, or Firm* — Ober, Kaler, Grimes & Shriver; Royal W. Craig

(57) ABSTRACT

A method and device for image guided dynamic radiation treatment of prostate cancer and other pelvic lesions including: 1) a unique fan geometry of radiation sources; 2) a special collimation method and apparatus to sculpt the radiation borders; 3) an integrated three-dimensional imager and a special tissue interface imaging system to locate and track critical boundaries in real-time; 4) a dynamic patient support system, which is shared by the said imager and the irradiation system; and 5) motorized custom shielding filters to further protect neighboring normal tissues such as the kidneys and femoral heads. The fan geometry utilizes a plural number of radiation sources arranged specifically for irradiating tumors in the human pelvis while not harming critical structures, and the collimation sculpts the radiation borders using motorized shields for different sensitive structures. This allows high doses of radiation to be delivered to lesions within the human pelvis, such as the prostate, while sparing its surrounding structures, such as the rectum and bladder, as well as the urethra that is contained inside the prostate.

13 Claims, 10 Drawing Sheets

Transverse View at A-A
(b)

Sagittal View
(a)

METHOD AND DEVICE FOR IMAGE GUIDED DYNAMIC RADIATION TREATMENT OF PROSTATE CANCER AND OTHER PELVIC LESIONS

CROSS-REFERENCE TO RELATED APPLICATION(S)

The present application derives priority from U.S. provisional patent application Ser. No. 61/210,766 filed 23 Mar. 2009.

BACKGROUND OF THE INVENTION (1) Field of the Invention

The present invention relates to a method and system for delivering radiation treatments to cancerous tissues within the human pelvis, such as the prostate gland and the cervix, while avoiding tissues that would otherwise be damaged by aggressive radiation treatment.

(2) Description of Prior Art

Radiation therapy and radiosurgery are established methods of treating patients with certain malignant and benign diseases. Radiotherapy is typically given over many episodes of treatment and generally involves treating larger volumes of tissue that often include normal structures that may be affected adversely by the radiation treatment. The strategy of spreading the therapy over many episodes separated in time is chosen to enable recovery of normal tissues included in the treatment volume. It is assumed that recovery of normal tissue occurs at a faster rate than that for cancerous tissue. Radiosurgery is typically given in one or a few episodes of very precise treatment to small volumes of diseased or affected tissue with the intent to destroy all tissue contained within the treatment volume.

Toxicity to normal structures limits the radiation dose and the treatment efficacy of both methods as normal structures may be contained within or adjacent to the diseased tissue. A normal structure within the prostate gland is the urethra. The normal tissues in proximity to the prostate gland are illustrated in FIGS. 2 & 3 and include but is not limited to the bladder and rectum as well as femoral heads and small intestine.

Prostate cancer is known to be slow growing and resistant to conventional treatment which is given by applying many small doses of radiation. Hypofractionation or a few large doses of radiation has been demonstrated to be more effective in killing cancerous cells for the same amount of energy deposited. However this approach causes unacceptable toxicities such as urethral stricture or even tissue necrosis. Although in theory we know that a higher daily dose is more effective for curing prostate cancer. However, daily dose greater than a 3Gy dose using external beam radiation has not been widely used because of urethra necrosis. Martinez et al. used radioactive seeds interstitially introduced to the prostate to deliver more than 10.5Gy daily dose to prostate and was found to be very effective. Vicini et al., High Dose Rate Brachytherapy In The Treatment Of Prostate Cancer, Journal World Journal of Urology, vol. 21, no. 4 (Sept. 2003), pp 220-228.

Because Vicini et al. used "peripheral loading", i.e., placing more radioactivity at the periphery of the prostate and avoiding high dose to the urethra, the toxicity from their interstitial high dose rate treatment was found to be low. However, their method has the greatest detriment of being very invasive and must be performed under general anesthesia. The present inventors do not know any method that can safely deliver a daily dose of greater than 3Gy using external beam radiation without damaging the urethra. Note that, although prostate cancer is used as an example, the method disclosed in this invention is not limited to the treatment of prostate cancer. There has not been any method that can safely deliver a high dose to the target while sparing a critical structure completely surrounded by cancerous tissue.

There is no treatment machine that can optimally spare the urethra and other critical organs such as rectum and, bladder and seminal vesicles. Conventional Modern radiotherapy employing intensity modulation techniques provides better dose conformity to the prostate and less dose to the bladder and rectum, with a typical dose distribution illustrated in FIG. 4, has enabled higher doses to the prostate by limiting the dose to structures surrounding the prostate but still gives high doses to the urethra. Therefore, hypofractionated radiation treatment for prostate cancer remains a dangerous procedure. For practical reasons such as treatment time and machine geometry, conventional treatment further has the limitation of approaching the prostate from a small solid angle and typically only transverse coplanar beams are used.

There is no dedicated tele-radiotherapy machine specifically designed to treat prostate cancer using a single or an arrangement of radioisotopes or other source of high energy radiation.

Protons have also been used for prostate treatment. This is an extremely expensive and complex method and has not demonstrated any benefit in part due to the challenges mentioned above for conventional treatment.

Past efforts of intensity-modulated radiation therapy have been limited to the use of compensators or multi-leaf collimators to modulate the incident radiation beams. The treatment beam arrangement is generally coplanar with the axis of rotation in the cranial caudal dimension.

In the present application the inventors describe a treatment device with unique beam geometry and collimation technology that can sculpt a radiation pattern avoiding the urethra and bladder and rectum while covering the prostate gland with a higher radiation dose.

Similar past efforts in image guidance have been limited to pretreatment imaging or treatment monitoring using simple planar X-ray fluoroscopy. Pretreatment imaging can include ultrasound, CT scanning, MRI and MV or kV planar X-ray. In the case of pretreatment imaging the tissues are not represented in real time during the treatment and changes that occur are not observed. In the case of X-ray fluoroscopy at the time of treatment imaging is limited to boney landmarks or implanted markers as surrogates for target tissues. In this invention we outline a technology and method to detect and monitor relevant soft tissue interfaces during radiation treatment.

Radiation therapy using external beams as described above and illustrated in FIG. 4 typically places the tumor at the isocenter, the intersection of all rotational axis. This arrangement makes patient set-up much easier. However, at any beam direction, radiation can only be directed at a point in the tumor through one unique path. This significantly limits the degree of freedom of how the tumor is irradiated. In this disclosure, we abandon the notion of a single isocenter and expand the control parameters of the treatment delivery to include the position of the treatment couch, which is fixed in all existing radiation treatments. The beams and the collimator still rotate around a point, but this point is no longer fixed in the patient. Thus, there is an abandonment of fixed isocenters inside the patient. Instead, maintaining a source rotational isocenter in the device is one of the key features of the present disclosure, a feature that has not been proposed or explored in radiation therapy.

Important features of the invention also include a practical method for real-time monitoring of the location of the critical structures and real-time adjustment of treatment parameters to spare these critical structures. This is again achieved through the extension of the definition of control points by associating with each control point a critical point of reference, which is a landmark on a critical structure that needs to be protected. For prostate treatment, we propose the use of an endorectal ultrasound probe to monitor the position of key interfaces, namely the urethra and the anterior rectal wall. For every control point that defines the treatment parameters at one time interval, there is a unique critical point of reference, which is normally the closest interface location. During delivery, the reference point for the next control point is updated during the delivery of the current control point based on the real-time imaging and real-time registration of the interface features between that acquired in real-time and that used for planning the treatment. Such updating of the locations of critical interfaces as the geometric reference of the control points allows the treatment to adapt to anatomy changes to protect the critical structures without changing the treatment plan.

Numerous clinical reports have established that the effects of radiation on urethra is a long-term process and the incidents of late effects increases with time over 20 years without a plateau. See, e.g., Miller et al., "Long-Term Outcomes Among Localized Prostate Cancer Survivors: Health-Related Quality-Of-Life Changes After Radical Prostatectomy, External Radiation And Brachytherapy", Journal of Clinical Oncology (Vol. 23, No. 12: 2772-2780). The slope of increase is directly proportional to the fractional dose delivered to the urethra. To date, there is no radiation treatment machine that can deliver high doses of radiation to the prostate while being able to spare the urethra.

In view of the foregoing, it is an object of the present disclosure to provide a method and an external irradiation system for delivering high doses of radiation to lesions within the human pelvis, such as the prostate, while sparing its surrounding structures, such as the rectum and bladder, as well as the urethra that is contained inside the prostate. The system would allow the radiation to be directed from a large number of beam directions through the arrangement of radiation sources and through the rotation of the radiation sources around the patient so as to achieve the maximal "cross-firing" effect. The system will also allow the treatment support structure to move dynamically so that the paths of the rays can optimally traverse the target in order to avoid the critical structures both internal and external to the target.

All radiation therapy treatment machines currently used for external beam radiation treatment are designed in such a way that the machine can deliver radiation to all tumor locations from a patient's head to a patient's toe. Such versatility is partly the reason that all external treatment machines used for irradiating prostate cancer externally uses only one radiation source. Although the source can be moved around to achieve "cross-firing" effect, practical considerations, such as the total treatment time and patient safety, limit the number of directions that the treatment can employ. Moreover, because all external beam treatment devices, such as the linear accelerators and Co-60 teletherapy machines, have a large treatment head required for shielding and collimation purposes, many beam angles cannot be used without causing a collision between the head of the machine and the patient.

In view of the above, we disclose a radiation machine design that utilizes a plural number of radiation sources arranged specifically for irradiating tumors in the human pelvis. In order to utilize all potential beam directions while not harming critical structures, the machine also contains motorized shields for different sensitive structures, including the rectum, femoral head, bladder, kidney, and testis. For different patients, these structures will be revealed by the three-dimensional images, such as CT and MRI, and the locations of these shields can then be customized for each individual patient.

It is well documented that the prostate gland changes location and shape within the pelvis relative to boney or surface landmarks between planning and treatment events. It is also recently documented that the prostate gland may change location and shape significantly during a typical 2-10 min episode of conventional radiation treatment. Court et al., Motion And Shape Change When Using An Endorectal Balloon During Prostate Radiation Therapy, Radiotherapy and Oncology, Volume 81, Issue 2, Pages 184-189.

Image Guided Radiation therapy today is limited to one of pretreatment ultrasound, planar x-ray, computed tomography or during treatment fluoroscopy. These approaches are used to define relative positions of internal structures to the radiation treatment isocenter using surrogates. Treatment fluoroscopy is limited to tracking implanted markers or boney landmarks and implementations generally have poor response times and so cannot be used to directly drive treatment or treatment modification. A key feature of the image guidance approach for this invention is that the device will use a combination of full 3D imaging, which require longer processing and feedback time, and boundary imaging, which only process and compare a small subset of the imaging signals for fast, real-time comparison and feedback. For the latter, only the tissues that define the boundary of the target and normal structure that we wish to avoid are imaged. The benefit of limiting the number of full 3D image acquisition and processing and only focusing on the interface between the target and the critical structure is the possibility to monitor the change in location and share of such critical interface in real-time. Such real-time monitoring would allow us to adapt the planned irradiation to such changes by changing the radiation beam angle and position relative to such boundaries. It will thus be possible to respond to any inadvertent or intended motion as part of the overall quality assurance of the treatment.

Other features, advantages and characteristics of the present invention will become apparent after the following detailed description.

SUMMARY OF THE INVENTION

Accordingly, it is an object of the present invention to administer high doses of radiation to lesions within the human pelvis, such as the prostate, while sparing its surrounding structures, such as the rectum and bladder, as well as the urethra that is contained inside the prostate.

In accordance with the foregoing and other objects, the present invention provides a method and device for image guided dynamic radiation treatment of prostate cancer and other pelvic lesions including: 1) a unique fan geometry of radiation sources; 2) a special collimation method and apparatus to sculpt the radiation borders; 3) an integrated three-dimensional imager and a special tissue interface imaging system to locate and track critical boundaries in real-time; 4) a dynamic patient support system, which is shared by the said imager and the irradiation system; and 5) motorized custom shielding filters to further protect neighboring normal tissues such as the kidneys and femoral heads. The fan geometry utilizes a plural number of radiation sources arranged specifically for irradiating tumors in the human pelvis while not harming critical structures. The collimation method and apparatus sculpts the radiation borders using motorized shields for different sensitive structures, including the rectum, femoral head, bladder, kidney, and testis.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

There has not been any prior art methods or devices described that can safely deliver high doses of radiation to the target(s) in the human pelvis while sparing a critical structure completely surrounded by cancerous tissue (example: the urethra in the prostate gland).

The present invention is a new device and method for delivering radiation to the human pelvis, such as the prostate gland, while avoiding irradiation of internal and external normal tissues. The device includes: 1) a unique fan geometry of radiation sources; 2) a special collimation method and apparatus to sculpt the radiation borders; 3) an integrated three-dimensional imager and a special tissue interface imaging system to locate and track critical boundaries in real-time; 4) a dynamic patient support system, which is shared by the said imager and the irradiation system; and 5) motorized custom shielding filters to further protect neighboring normal tissues such as the kidneys and femoral heads.

Figure 1:
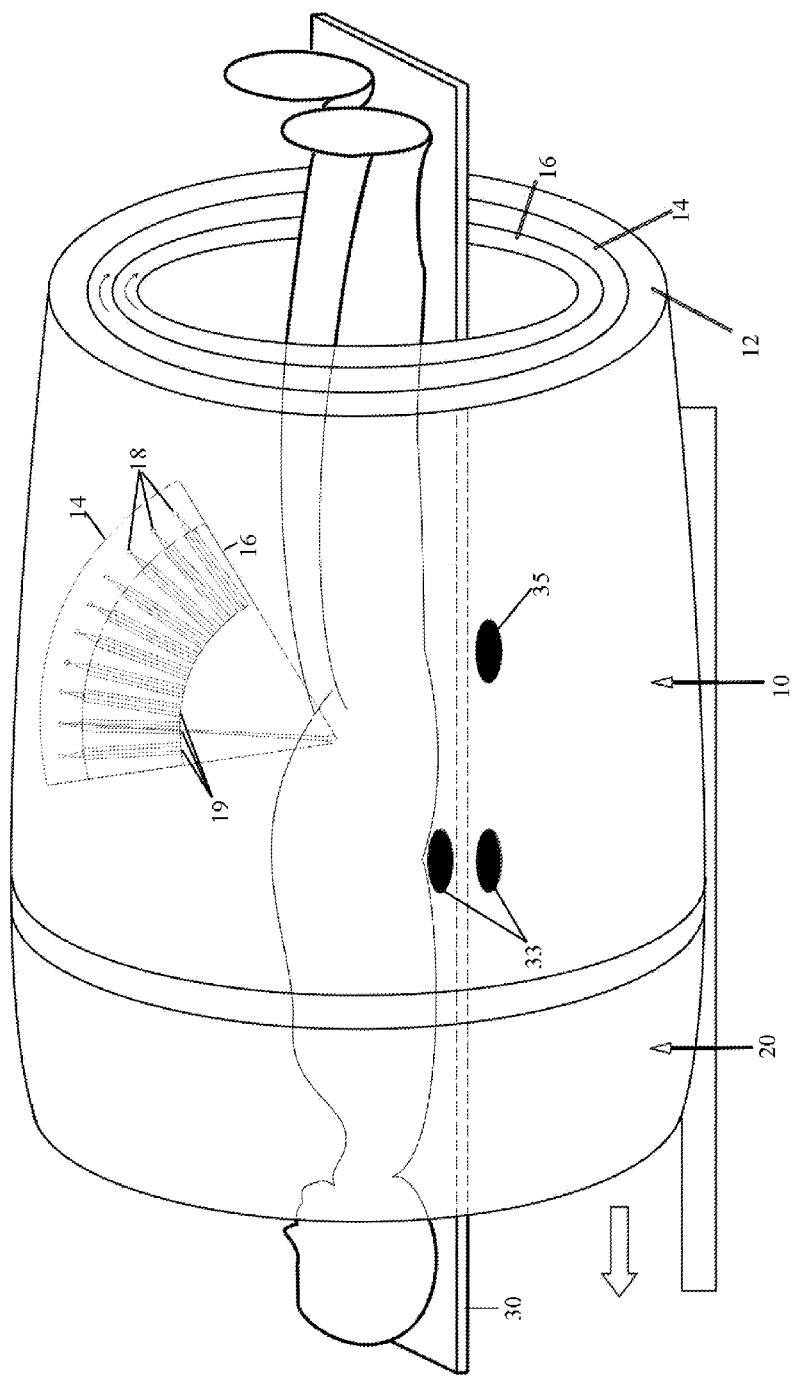
FIG. 1 is a schematic design of the prostate/pelvic irradiation system.
Figure 2:
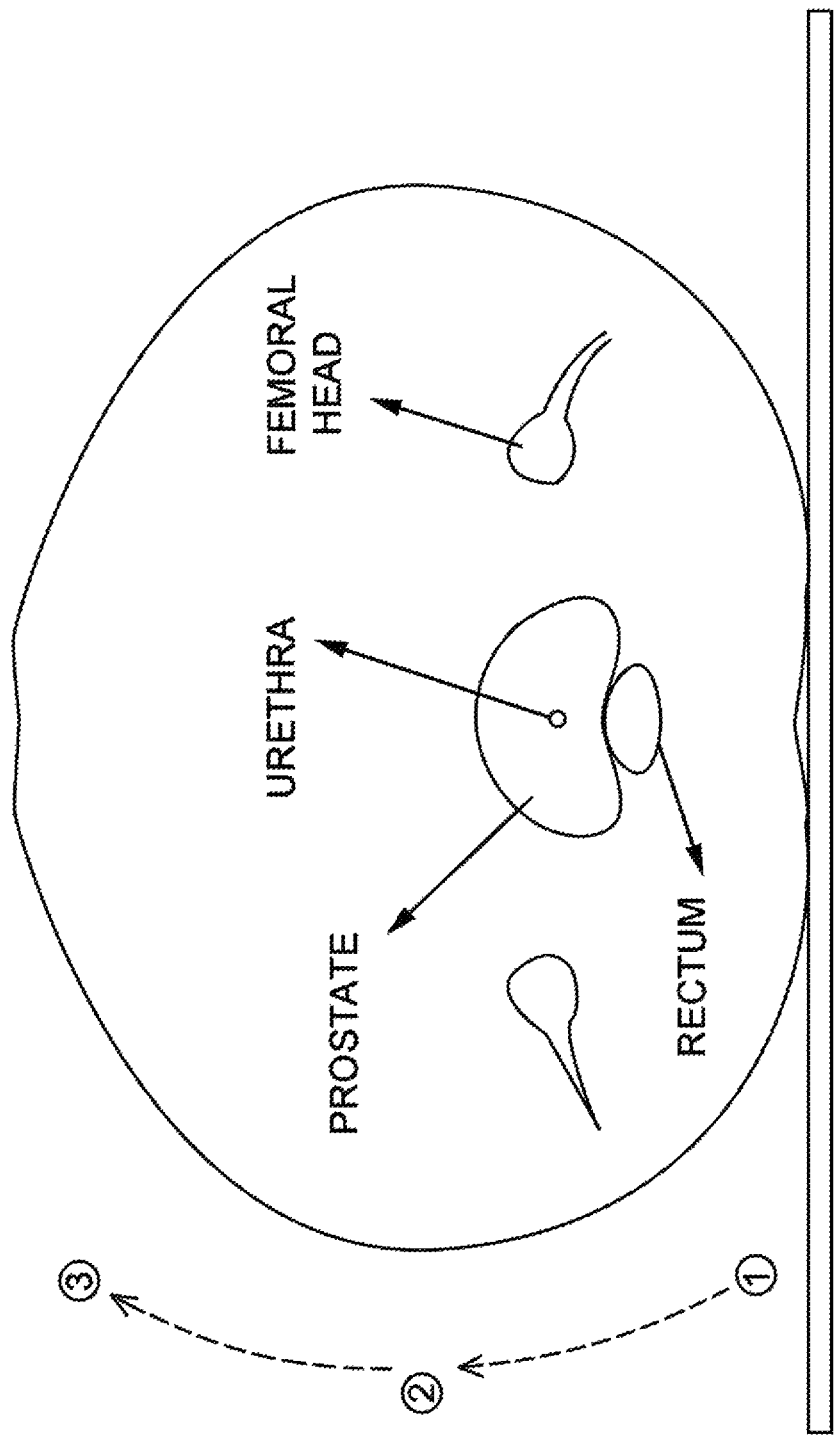
FIG. 2 is a transverse cross section of a representation of the internal organs of the male pelvis showing generalized relative position of the prostate and surrounding normal structures that must be avoided during radiation treatment.
Figure 3:
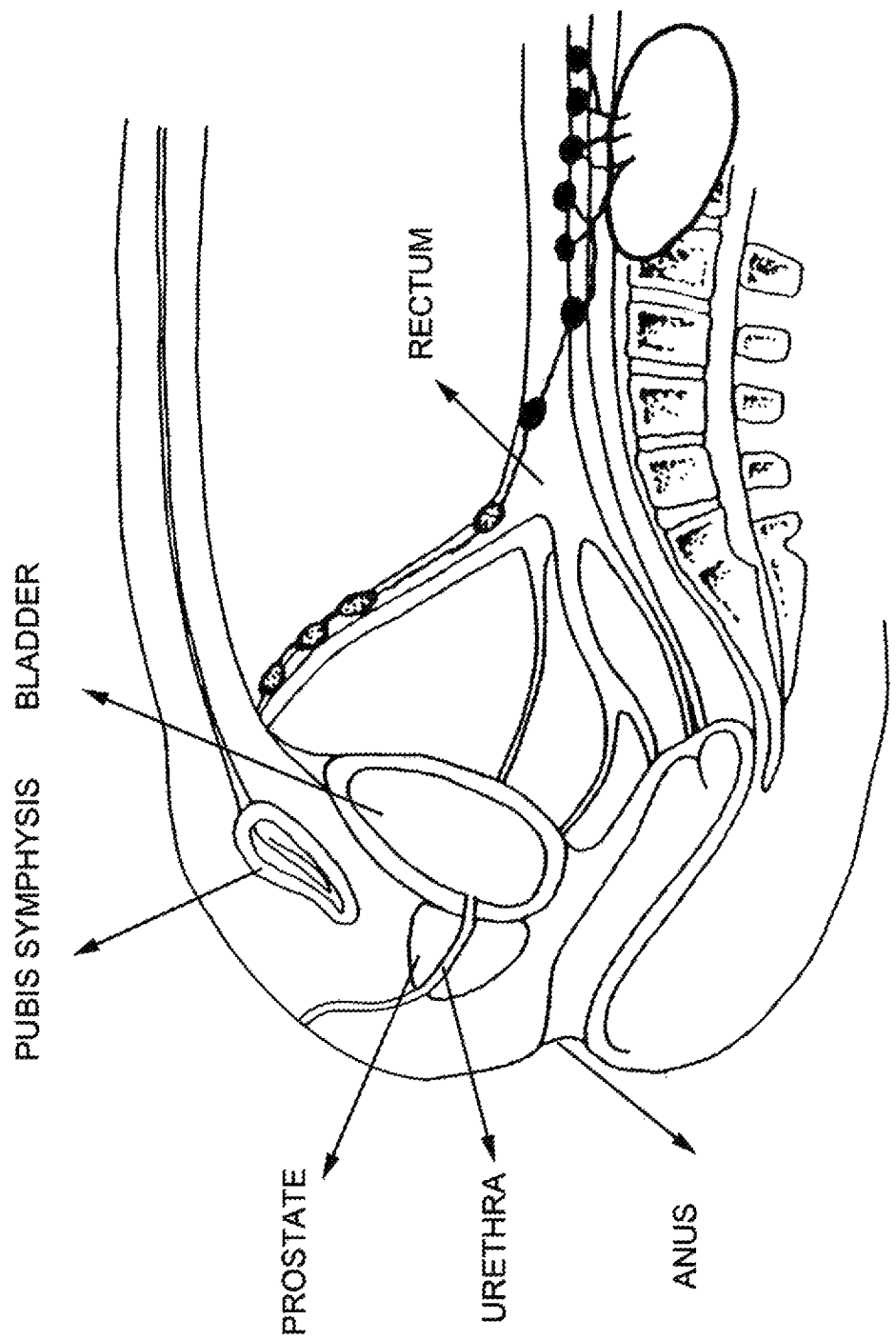
FIG. 3 is a sagittal cross section of a representation of the internal organs of the male pelvis showing generalized relative position of the prostate and surrounding normal structures that must be avoided during radiation treatment.
Figure 4:
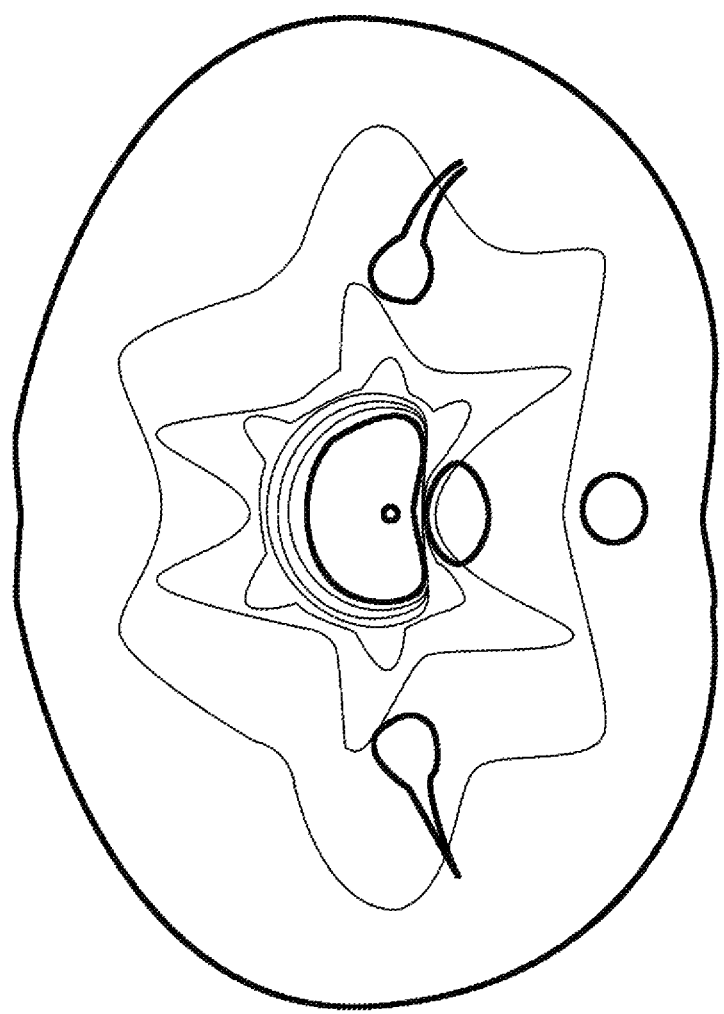
FIG. 4 is a radiation beam arrangement using 6 radiation fields and resultant dose distribution for a typical prostate treatment employing modern intensity modulated radiation therapy (IMRT) technology covering the whole gland. The isodose lines from inner most to the outermost represent 90% to 40% in 10% increments.

A schematic design of the prostate/pelvic irradiation systems is illustrated in FIG. 1. The system generally comprises two main components: an irradiation delivery system 10 and an imaging system 20. The imaging system 20 can be a CT or MRI, having a regular cylindrical doughnut shape. The patient lying on a couch 30 is driven through the center aperture of the "doughnut". The irradiator 10 is in the shape of a tapered doughnut, with a hollow central space for the couch 30 and the patient's lower body to pass inside. The narrow end of the irradiator 10 is in the direction of the patient's feet. The taper can take the shape describable by a mathematical function such as a cone, sphere or parabola or take any other irregular shape that can accommodate both the radiation source geometry and the contour of the human body. The imager 20 controls the couch 30 movement during imaging. The irradiator 10 controls the couch 30 during treatment. However, the coordinates of the couch 30 are known by both the imager 20 and the irradiator 10 at all times. The dynamic patient support is an imaging/treatment couch 30, which can make dynamic movements in all three dimensions during radiation delivery. Although the focal spot of the radiation beams are fixed on the central axis, the focal spot can fall onto different positions inside the prostate or a pelvic lesion, by controlling the position of the treatment couch 30.

According to a preferred embodiment, the irradiator 10 comprises three concentrically mounted shell structures (See FIG. 1). The outermost ("outer shielding") shell 12 serves to provide radiation shielding. The middle ("source") shell 14 carries at least one row of radiation sources 18 (see inset) arranged in a unique fan geometry specifically for prostate/pelvic irradiation (described below with reference to FIG. 5). The innermost ("collimator") shell 16 carries the same number of collimator holes 19 (see inset) geometrically arranged to align with all the sources 18.

The radiation sources 18 can either be man-made radiation sources such as x-rays from a high energy x-ray machine or linear accelerators or radionuclide, such as Cobalt-60. In the preferred embodiment, more than one source 18 is used, although the use of a single source should also be possible. In the preferred embodiment, a number of radiation sources 18 and individual collimators 19 are arranged on an arc (see FIG. 5). The principle axes of all sources 18 are directed to a single point P on the central axis to achieve a focusing effect. The source 18 series need not be a strict coplanar arc but should be generally aligned in the superior inferior direction. When all the sources 18 are at a fixed location, i.e., the beams that form the "fan" stay at a fixed rotation angle, the focal point P receives N times the amount of radiation as compared with the surrounding normal structures, where N is the number of sources. As the sources and the collimators are rotated together under the control of a central control system, the time duration of a surrounding normal structure being under the beam becomes a very small fraction of the total irradiation time, while the target is always under intense irradiation. From the focal point P, the radiation beams will continue to traverse the patient and exit the patient to hit the concentric shells on the opposite side of the patient. The shell structure on the opposite side of the patient thereby also serve as the additional radiation shielding material. If needed, lead or tungsten blocks can also be placed to block the path of radiation, making the irradiation system a self-shielded unit.

When a radionuclide is used as the radiation source, the collimator shell 16, i.e, the innermost shell, should also carry the same number of shielding blocks, made of high density material such as tungsten, also arranged in the same pattern as the collimators 19 but offset the collimators 19 by a fixed rotating angle (or a fixed translation). With a relative rotation (or motion) of the collimator shell 16, these blocks align with all the sources 18. Therefore, that the radiation sources 18 can be switched from aligning with collimator holes 19 to aligning with block by a relative rotation of the two inner shells 12, 14, providing an effective beam "on" and "off" mechanism. A thin fixed and non-rotating protective shield, made of light material such as aluminum and or plastic, may be placed inside the collimator shell for patient safety (not shown in FIG. 1).

Not all collimators 19 are necessarily driven together. In an alternative embodiment, each of the collimators 19 can be driven individually between "on" and "off" positions, aligning either the collimator hole 19 or the solid block with the corresponding radiation source 18. For the directions where some of the beams from the row of sources 18 are needed but the others are not desirable, the others can be turned off by switching them to the "blocked" position, allowing only a subset of radiation beams to enter the patient.

Because the sources 18 are distributed on a plane substantially parallel to the patient axis, the irradiation device does not have to be in the multiple concentric tapered structure. In an alternative embodiment, the source—collimator complex can be mechanically coupled to the outer shell as a single block, and driven to rotate around the patient. In this embodiment, the outer shell 12 serves as both the shielding material and the ring-shaped supporting structure for the beams to rotate around the patient. In such embodiment, a beam-stop can be mounted on the opposite side of the patient to block the path of the radiation beams. Such beam stop should also be driven to rotate in synchrony with the radiation sources for effective shielding at all times.

The rotation of the row of sources 18 around the patient does not need to be always 360 degrees, and the speed of rotation does not have to be constant. The row of sources 18 can rotate a full circle, or a partial circle, or rotate back and forth over a small angular interval during radiation delivery as dictated by the treatment plan.

Figure 5:
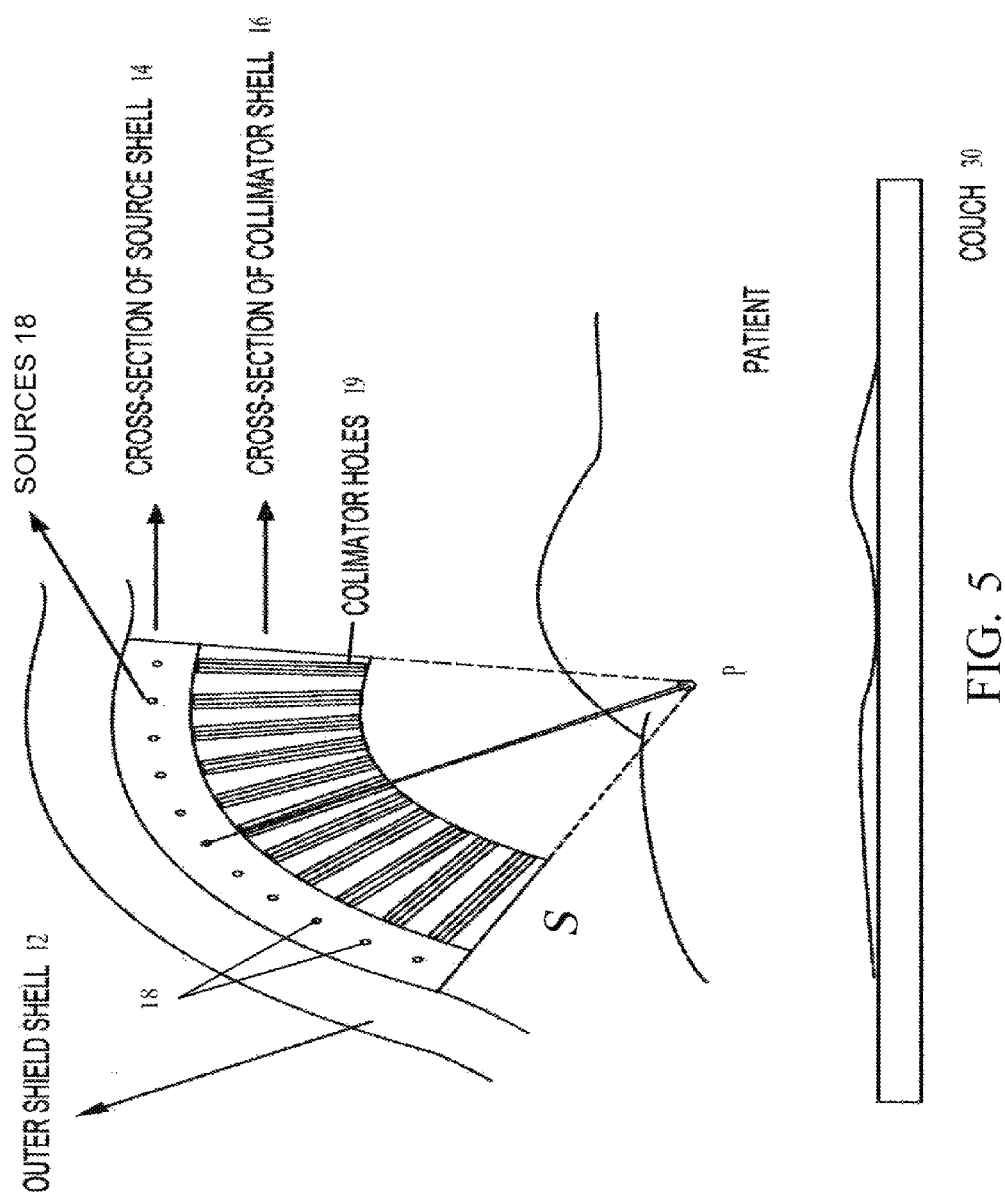
FIG. 5 is a sagittal cross-section of a generalized patient in position under the fixed arc of sources showing the asymmetry of the source arc.

The arrangement of the radiation sources 18 is unique, specifically for irradiating lesions in the human pelvis. Because the belly-buttocks region is the thickest, and the leg portion is thinner, the radiation sources 18 are arranged asymmetrically with respect to the vertical axis, as shown in FIG. 5. More than one row of sources 18 can optionally be used, with each row of sources distributed on a plan substantially parallel to the patient axis (i.e., the z-axis). If more than one row of sources 18 are used, the multiple rows are packed closed together in a very narrow angular interval, and all sources 18 point to the common focal point with the beam edges aligned. Optionally, multiple rows of sources 18 can be distributed on the opposing sides (180 degrees apart). However, on each side, all the sources 18 must be packed close to one plane. This arrangement maintains the fan-like dose pattern in the patient which is a key feature required to efficiently sculpt the dose distribution and provides greater freedom for the computer to optimize the angular weightings of the fan-shaped radiation beams.

Inside the concentric conical shells 12-16 is a conical space to accommodate the patient's lower body. The patient is supported by the imaging/treatment couch 30, which can make dynamic movements in all three dimensions during radiation delivery. Although the focal spot P of the radiation beams are fixed on the central axis, the spot can fall onto different positions inside the prostate or a pelvic lesion, by controlling the position of the treatment couch 30.

Figure 6:
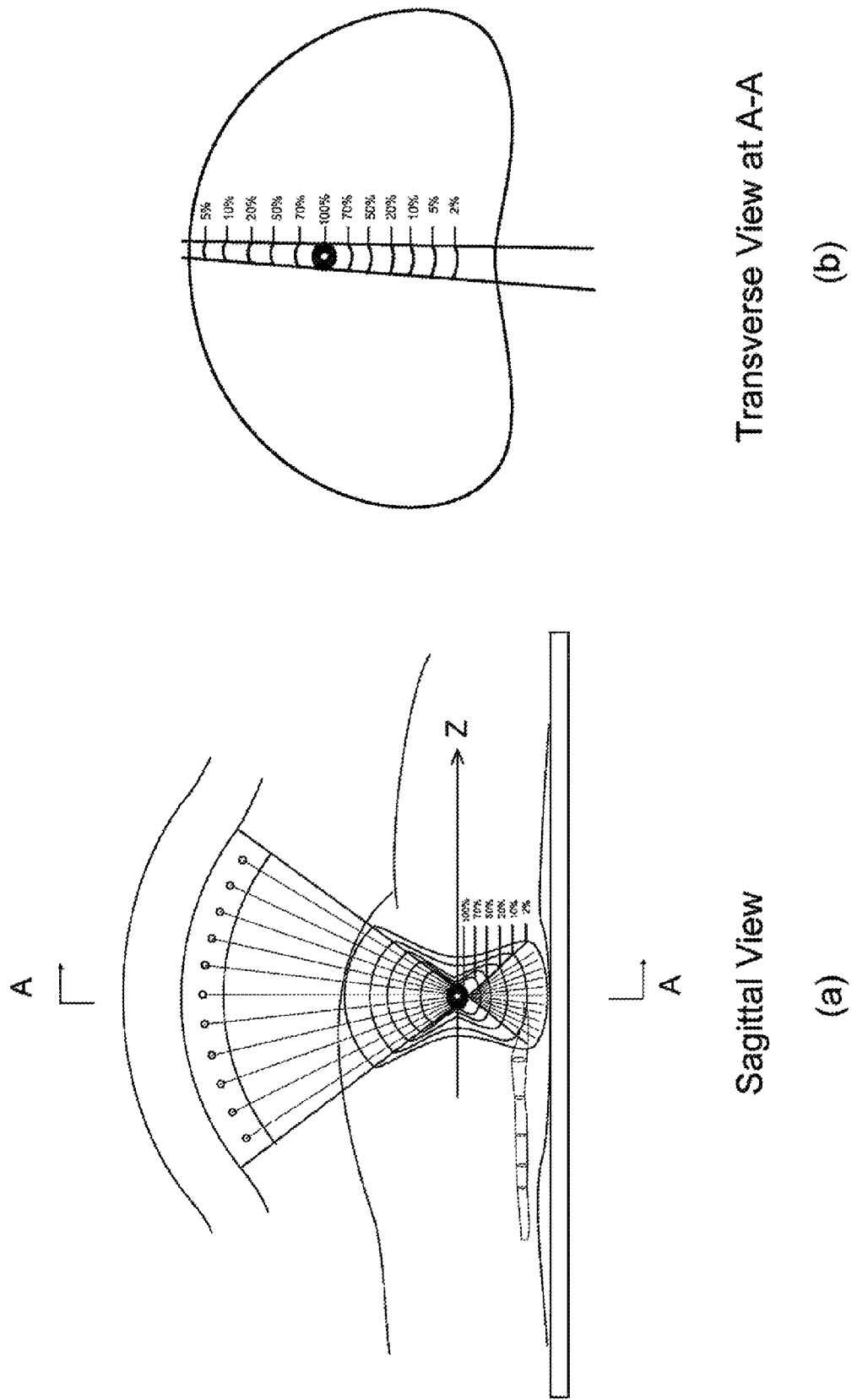
FIG. 6 illustrates the isodose levels from the fan-shaped source geometry, like a butterfly in the plane of sources (a), but narrow in the transverse plane (b).

Note that unlike most radiosurgery devices proposed or in practice, the dose pattern at the focal point P does not resemble a sphere. But rather, the dose pattern created by all the radiation beams resembles a butterfly, with the body of the "butterfly" at the focal spot where the radiation intensity is the highest. As the sources are fixed at a rotational angle, only a thin, sagittal slice is irradiated. The thickness of the slice on the average is the same as the focal spot size, which ideally is less than 2 cm. FIG. 6 (a) shows the radiation dose distribution in a patient on the sagittal plane that intercepts the sources and the focal point. This plane also contains the z-axis (the patient axis). As seen from FIG. 6 (a), the dose is the highest at the focal center, and falls off both towards the sources and away from the sources. The dose falls off slower on the beam entry side of the focal point and faster on the beam exit side of the focal point. This phenomenon is caused by two competing factors: 1) the decrease of beam intensity of each beam as a function of distance from the source and attenuation in the patient; and 2) the increase of beam intensity as all the beams come closer towards the focal point and apart again after exiting the focal point. In terms of magnitude, the second factor dominates. On the beam entry side of the focal point, these two factors have opposite effects although the second factor dominates. On the beam exit side both factors have the same effect to drive the fast dose fall off with distance. FIG. 6 (b) shows the same dose distribution as above but on a transverse plane of the patient. Only a very narrow strip on this plain is irradiated when the sources are at one rotational angle.

The butterfly shaped dose distribution of FIG. 6 described above can be rotated about the z-axis of the irradiation unit, which is parallel to the axis of the patient. The rotation does not necessarily need to be at a constant rate or along the same direction. The amount of time that the sources stay at an angle varies based on the desirability of irradiating through this angle, as dictated by the treatment plan, which is computer optimized together with the couch positions.

Referring back to FIG. 6 (b), the fact that each source rotation angle irradiates just a sagittal slice with an elongated focal center of high dose is a key feature for sculpting the dose in the patient. By moving the patient dynamically during irradiation, we can not only put the focal spot at any position in the patient, we can also orient the thin slice in any orientation to achieve the desired overlap. Because both the location of the focus and the orientation of the butterfly-shaped dose distribution can be optimized with a computer, the amount of freedom as compared with any known radiation treatment devices is much greater. At each moment during delivery, the parameters of the delivery are described as control points, the same as for conventional radiation treatment delivery using linear accelerators. However, unlike the linear accelerator, each of these control points also specifies the location of the focal point (set through patient couch motion), in addition to the beam angle.

Figure 7:
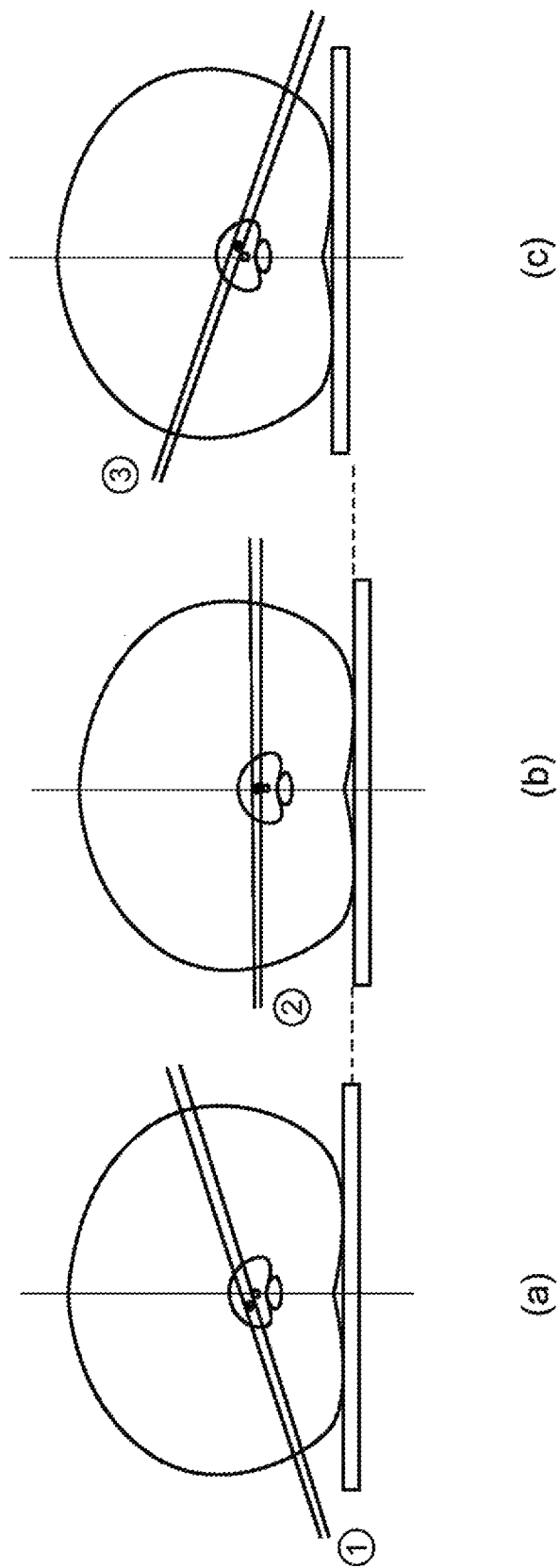
FIG. 7 illustrates three control points at three instances where the couch is at different positions and the beams at different angles. The critical point of reference is the center of the urethra so that it can be spared.

FIG. 7 shows three control points during radiation delivery as an example of how the thin slices of the butterfly-shaped radiation dose pattern can be arranged to deliver dose in the prostate while sparing the urethra. The open circle indicating the urethra and the dark dot in the beam line indicates the focal spot of all the beams from all the sources. Each of the three control points specifies a unique set of beam angle and couch position such that the focal point is located adjacent to, but does not does not overlap, the urethra. All three control points can use the center of the urethra as the critical point of reference.

Figure 8:
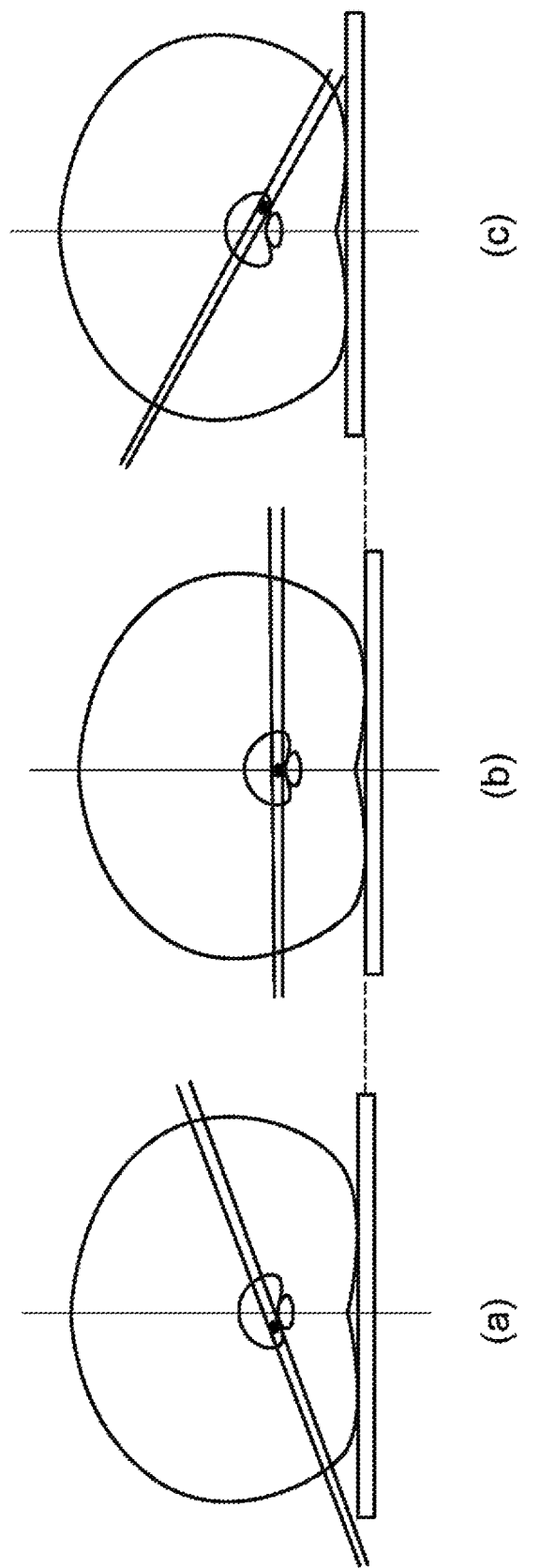
FIG. 8 is similar to FIG. 7 except that the critical point of reference is the anterior rectal wall.

FIG. 8 illustrates how the thin slices of the butterfly-shaped radiation dose pattern can be arranged to spare the rectum, with each control point specifying both the beam orientation and the focal spot position. The present method is distinguished from existing external beam radiation treatments where the patient is fixed and the center of beam rotation is also fixed with respect to the patient. The reasonable critical points of reference in these control points should be located at the anterior rectal wall. Although the focal spot is fixed at the center of source rotation, it is not fixed with respect to the patient. By setting the couch 30 positions differently, the focal point can be located at any position inside the human pelvis, and the beam orientation at which the focal dose is delivered can also be optimized to avoid the critical structures.

In order for the delivery to be uninterrupted, all he control points defining the treatment delivery are geometrically connected, i.e., moving from one control point to the next is physically achievable and the constraints of mechanical movement is not violated. Optimizing the control points using the freedom afforded by the method disclosed above and ensuring the successive control points are connected are the tasks of the treatment planning system. Computer optimization algorithms similar to that used for current external beam radiation therapy will be employed to optimize the control points subject to the mechanical motion constraints. What distinguishes this treatment system from the existing ones is the geometric point of reference, In all existing treatment plans defined by control points, all control points has a common point of reference, typically the radiation isocenter of rotation. By not using a fixed isocenter, each control point is referenced to another point defined by the registered images as described in the following sections. This feature allows the delivery to adapt to real-time anatomical changes without redefining the control points. For example, if the real-time imaging system reveals that the anterior rectal wall moved up by 5 mm because of gas build-up in the rectum during treatment, all the control points designed to spare the rectum will be automatically moving the focal spot up by proper distance because their points of reference are on the rectal wall.

Figure 9:
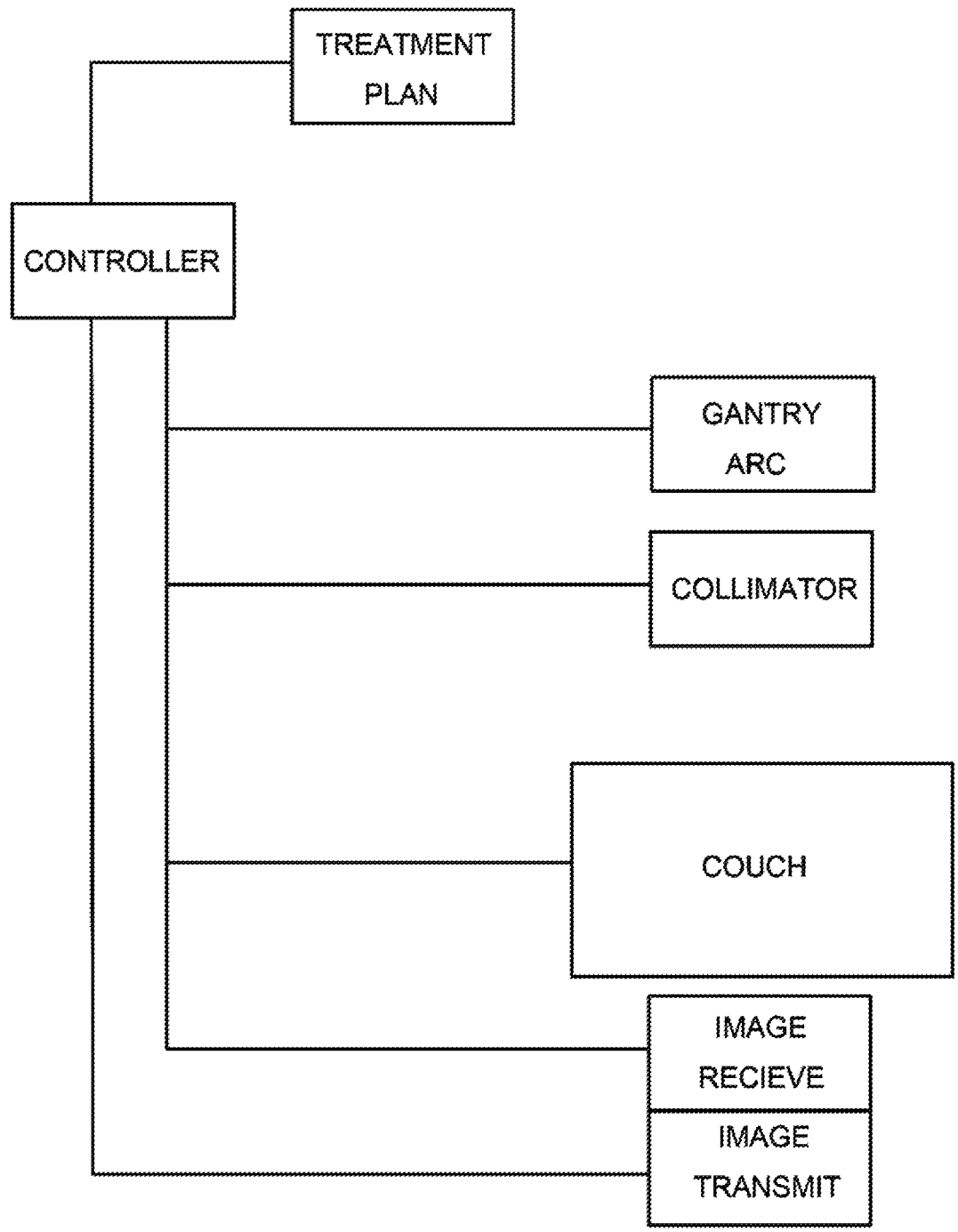
FIG. 9 illustrates the control system architecture of the present invention.

This entire system including both imaging and radiation delivery is managed using real time system control technology so that the position of the fan of radiation beams and collimator can be dynamically coordinated with the position of the target tissues using feedback from the real time tissue interface imager and dynamic patient support that can translate in three dimensions to place the correct tissues at the center of rotation of the collimated beams. The system control architecture is illustrated in FIG. 9. The imager is the trigger for all other components during treatment. The imager determines a specific components state including the gantry, couch position and collimator which can be dynamically adjusted to the critical point of reference that is being monitored a each moment during treatment.

The system further incorporates a pre treatment imaging unit. The imaging unit can be a CT or MRI, both of which are of a "doughnut" shape. The imaging unit is placed in front of the irradiation unit thereby allows the sharing of the same patient supporting couch, that can translate from the imaging section to the treatment section, which can also be shaped as a "doughnut" or with a hollow space for the patient's lower body to be placed inside so that the prostate or other lesions in the pelvis can be aligned with the center of the radiation beam(s). The patient lying on the table gets a CT or MRI scan before entering the irradiation section at the end of the device. The MRI or CT unit can be fixed with the irradiation unit or it can be separated and can slide away on a rail to allow the patient's upper body and head not to be enclosed for patient comfort.

Because the imaging table and the treatment table is shared, and the imager and the irradiation machine have a fixed geometric relationship, the coordinates of the volumes of interest, such as the tumor and its surrounding critical structures, revealed by the three-dimensional (3D) images can be directly translated to the treatment machine. The orientation and the location of the ultrasound probe used for real-time monitoring of the tumor-critical structure interface or the urethra position are also revealed by the imaging unit. After the 3D CT or MRI images are acquired, a 3D ultrasound image set is also acquired. Because the geometric relationship between these two 3D image sets are known and fixed, the points corresponding to locations in the patient between these two images have a one-to-one fixed relationship. That is, these two image sets are automatically registered.

The 3D image set is transferred to a treatment planning system that derives the dynamic treatment plan that defines a set of geometrically connected control points. Each control point defines, at the minimum, the couch position or coordinates, the beam angle, the amount of time required to move from the previous control point to the present control point, and a critical point of reference. The critical point of reference is the interface point between the tumor and a critical structure that is closest to the radiation beam of the current control point. The optimized final treatment plan is transferred to the central control unit of the treatment delivery system for execution.

Figure 10:
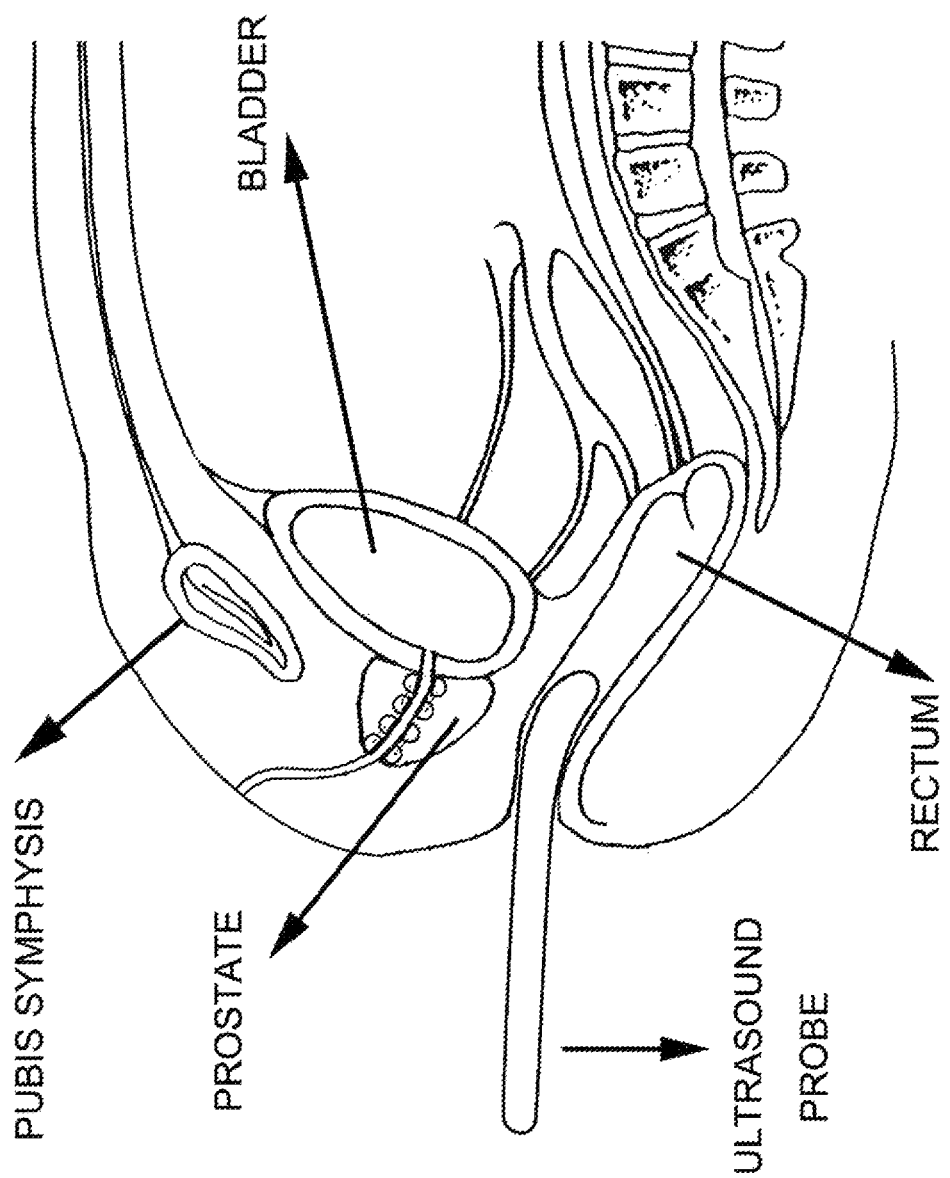
FIG. 10 shows a sagittal cross-section of the prostate gland and rectum showing the ultrasound probe and urethra.

In order to monitor the position of critical tissue boundaries a real-time method of imaging is a key feature of the external beam treatment device described in this disclosure. The proposed method represented in FIG. 10 uses a line of ultrasound transducer elements that can be inserted inside the patient's rectum and be positioned posterior to the prostate gland. This device is geometrically calibrated to the treatment beam using a mechanical locator. The imaging system is optimized to selectively sense the rectal/prostate, prostate/urethral and prostate/bladder boundaries. Only one boundary is focused at a time which coincides with the time that the radiation is being applied near to this critical boundary.

During treatment delivery, the ultrasound reveals, in real-time, the two-dimensional image containing the critical point of reference for the next control point to be delivered. Although the ultrasound imager is capable of 3D imaging, we suppress the volume to only image the interface of interest that contains the next critical point of reference. Such limited volume allows real-time comparison between the image of the area acquired before treatment and that acquired at each moment. If changes are noted, the new location of the critical point of reference for the next control point will be determined, and updated. Because all the control points are referenced to their own critical point of reference, the same geometric relationship between the radiation beam and the critical point of reference is kept as planned. Such positional correction is accomplished with the combination of patient couch translation and radiation beam angle adjustment (rotation).

As shown in FIG. 1 the patient lies supine on the dynamic table with his feet towards the fixed arc treatment isocenter. The ultrasound probe is placed inside the patient's rectum (FIG. 10) and connected to the imaging control system. The table top can slide inside a covered space protecting the patient from the moving parts directing the treatment beams. The contoured shape of the covered tube follows the pelvis and narrows over the legs. This allows an asymmetric angular range of radiation sources (FIG. 5) while maintaining full collimation length across the arc which is optimized to minimize the irradiation of the structures anterior to the prostate gland.

The radiation beams are collimated with a set of collimators of proper size and shape for prostate treatment. The beam size is determined by balancing the treatment efficiency, i.e., treatment time, and the ability to sculpt fine structures such as the urethra and the rectum. It is important that the collimator is capable of creating a sharp dose gradient at its beam boundary. This ability is analogous to a sharp knife, capable of sculpting an intricate high dose volume with complex shapes.

To customize or personalize treatment protective elements of this device include radiation shields 33, 35 (FIG. 1) that may be positioned inside the protective tube. For example, shields 33 are translated to cover the kidneys, shields 35 the femoral heads, and similar (unshown) for the testis. As the radiation sources 18, pass in front of these structures the shields 33, 35 are positioned to block the path of the radiation before it can enter the patient.

All patents, patent application publications, journal articles, textbooks, and other publications mentioned in the specification are indicative of the level of skill of those in the art to which the invention pertains. All such publications are incorporated herein by reference to the same extent as if each individual publication were specifically and individually indicated to be incorporated by reference.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

What is claimed is:

1. A radiation machine for treating a patient having prostate or pelvic lesions, comprising:
   an irradiator defining a hollow interior, and including,
      a barrel-shaped three-layer shell structure having a circular axial cross-section and an arcuate sagittal cross-section defining a hollow interior, said shell structure having three separate layers including an innermost collimator layer, an outermost shield layer, and a middle source layer,
      a plurality of radiation sources arranged in one or more rows inside the middle source layer of said shell structure along the sagittal arc of said irradiator to provide a plurality of radiation beams traversing the hollow interior of said irradiator in a fan geometry of radiation that converges from said sagittal arc to a focal point in said patient having pelvic or prostate lesions,
      a plurality of collimators in the innermost collimator layer of said shell structure, each of said plurality of collimators being aligned with a corresponding one of said plurality of radiation sources for directing its radiation beam to the said focal point,
      the outermost shield layer of said three-layer shell structure comprising a radiation shield to block the plurality of radiation beams from leaking outwards,
   a dynamic patient support system within the hollow interior of said irradiator; and
   an annular 3D imaging scanner having a circular axial cross-section defining a hollow interior and physically coaxially connected to said irradiator for guidance of radiation delivery.

2. The radiation machine according to claim 1, further comprising one or more motorized shields configured to be positioned between the patient and said innermost collimator layer of said shell structure that shields critical structures.

3. The radiation machine of claim 1, in which said innermost collimator layer of said shell structure includes a plurality of radiation blocks each geometrically offset in position from a corresponding collimator hole, said radiation blocks and collimator holes being alternately alignable with said radiation sources for blocking said plurality of radiation beams, whereby said plurality of radiation sources can be switched from an open position to a blocked position, and vice versa, by a relative motion between the innermost collimator layer and middle source shell.

4. The radiation machine of claim 1, in which said plurality of radiation sources is one of a linear accelerator or a radioactive material.

5. The radiation machine of claim 1, wherein said 3D imaging scanner is configured for transferring a 3D image set to a treatment planning system.

6. The radiation machine of claim 5, further comprising a real-time ultrasound imager operable in combination with said 3D imaging scanner for registering tissue interfaces between ultrasound images and said 3D image set for allowing said irradiator to maintain said focal point at an intended location.

7. The radiation machine of claim 1 where the 3D imaging scanner is connected by rails to said irradiator and is slidable relative thereto for improved patient comfort.

8. The radiation machine of claim 1, in which said one or more rows of radiation sources are configured to be asymmetrically positioned around a patient's buttocks-to-leg joint for more efficient radiation penetration to pelvic and prostate structures.

9. The radiation machine of claim 1, in which the one or more rows of radiation sources is configured to be rotated together with said collimators around the patient 360 degrees.

10. The radiation machine of claim 1, in which the patient support system is configured to be dynamically moved in three linear dimensions in coordination with rotation of said plurality of radiation beams during radiation delivery to position said focal point of the fan geometry of radiation beams at any location inside the patient and to prevent a plane of said fan geometry from traversing critical structures.

11. The radiation machine of claim 1, in which said one or more rows of radiation sources is positioned along an arc that is asymmetric relative to a transverse plane across said focal point.

12. The radiation machine of claim 1, in which said one or more rows of radiation sources further comprises multiple rows of radiation sources, all of the radiation sources along each row being configured to be aligned substantially parallel to the patient.

13. The radiation machine of claim 1, in which said one or more rows of radiation sources further comprises multiple rows of radiation sources located on opposing sides of the radiation machine, said multiple rows of radiation sources being substantially coplanar so that the fan geometry of the radiation can be maintained.

* * * * *